(12) United States Patent
Innocenti

(10) Patent No.: US 7,677,403 B2
(45) Date of Patent: Mar. 16, 2010

(54) GLUED OR HEAT-SEALED CAP FOR RESEALING TEST TUBES FOR CLINICAL ANALYSES

(75) Inventor: Carlo Innocenti, Bologna (IT)

(73) Assignee: ECOCAP's S.R.L., Casalecchio di Reno (IT)

( * ) Notice: Subject to any disclaimer, the term of this patent is extended or adjusted under 35 U.S.C. 154(b) by 140 days.

(21) Appl. No.: 10/572,100

(22) PCT Filed: Feb. 24, 2004

(86) PCT No.: PCT/IT2004/000082

§ 371 (c)(1),
(2), (4) Date: Mar. 16, 2006

(87) PCT Pub. No.: WO2005/025750

PCT Pub. Date: Mar. 24, 2005

(65) Prior Publication Data

US 2007/0028704 A1    Feb. 8, 2007

(30) Foreign Application Priority Data

Sep. 18, 2003  (IT) .......................... BO2003A0542

(51) Int. Cl.
*B65D 41/14* (2006.01)
(52) U.S. Cl. ...................... 215/326; 215/327; 215/319; 215/349; 215/351; 435/287.4
(58) Field of Classification Search ................ 215/326, 215/327, 310, 311, 319, 349, 350, 351, 253; 435/287.4
See application file for complete search history.

(56) References Cited

U.S. PATENT DOCUMENTS

| | | | | |
|---|---|---|---|---|
| 2,287,746 A * | 6/1942 | Morton | ....................... | 215/307 |
| 2,897,992 A * | 8/1959 | Nungester | .................... | 215/293 |
| 3,437,224 A * | 4/1969 | Williams | ..................... | 215/307 |
| 3,552,591 A * | 1/1971 | Wimmer | ..................... | 215/247 |
| 3,640,418 A * | 2/1972 | Williams | ..................... | 215/354 |
| 4,066,511 A * | 1/1978 | Montagnon | .................. | 435/34 |
| 4,254,884 A * | 3/1981 | Maruyama | .................. | 215/232 |
| 4,345,028 A * | 8/1982 | Nelson et al. | .................. | 435/30 |
| 4,370,190 A * | 1/1983 | Ichinose et al. | .......... | 156/307.3 |
| 4,461,837 A * | 7/1984 | Karle et al. | ............... | 435/287.4 |
| 4,863,453 A * | 9/1989 | Berger et al. | ................ | 604/415 |
| 4,961,986 A * | 10/1990 | Galda et al. | ................ | 428/201 |
| 5,057,365 A * | 10/1991 | Finkelstein et al. | ......... | 428/344 |
| 5,061,263 A * | 10/1991 | Yamazaki et al. | ........... | 604/403 |
| 5,252,484 A * | 10/1993 | Matner et al. | ............ | 435/287.4 |
| 5,418,167 A * | 5/1995 | Matner et al. | ............ | 435/287.4 |
| 5,622,745 A * | 4/1997 | Sloan et al. | ................... | 427/2.1 |
| 5,915,577 A * | 6/1999 | Levine | ....................... | 215/232 |
| 6,001,087 A * | 12/1999 | Zurcher | ...................... | 604/411 |
| 6,006,933 A * | 12/1999 | Henning et al. | ............. | 215/328 |
| 6,361,505 B1 * | 3/2002 | Rainen et al. | ............... | 600/577 |
| 6,361,744 B1 * | 3/2002 | Levy | ........................... | 422/99 |
| 6,382,441 B1 * | 5/2002 | Carano | ...................... | 215/247 |
| 6,623,955 B2 * | 9/2003 | Matner et al. | ............ | 435/287.4 |
| 6,806,094 B2 * | 10/2004 | Anderson et al. | ........... | 436/180 |

(Continued)

*Primary Examiner*—Anthony Stashick
*Assistant Examiner*—Christopher B McKinley
(74) *Attorney, Agent, or Firm*—Egbert Law Offices PLLC

(57) ABSTRACT

This invention refers to a glued or heat-sealed cap for resealing test tubes for clinical analyses which can be easily perforated and permits the application of a second cap.

1 Claim, 3 Drawing Sheets

U.S. PATENT DOCUMENTS

| | | | |
|---|---|---|---|
| 6,893,612 B2 * | 5/2005 | Kacian et al. | 422/100 |
| 6,974,045 B1 * | 12/2005 | Trombach et al. | 215/232 |
| 7,294,308 B2 * | 11/2007 | Kacian et al. | 422/99 |
| 7,422,782 B2 * | 9/2008 | Haedt et al. | 428/41.7 |
| 2002/0079284 A1 * | 6/2002 | Carano | 215/247 |
| 2005/0198925 A1 * | 9/2005 | Perlman | 53/426 |
| 2007/0034592 A1 * | 2/2007 | Pavlovic et al. | 215/253 |

* cited by examiner

GLUED OR HEAT-SEALED CAP FOR RESEALING TEST TUBES FOR CLINICAL ANALYSES

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention pertains to a cap for RESEALING test tubes for chemical analyses after they have undergone processing in automatic or manual clinical chemical analyzers.

BACKGROUND OF THE INVENTION

It is known that the analysis of bodily fluids usually takes place in a general clinical laboratory. The sample, for example, blood taken from a vein, is collected in a test tube which is capped and labeled and then sent to a laboratory, where the contents are analyzed using suitable apparatuses, with or without the addition of reagents.

At this point the analysis could be considered terminated if challenges to or doubts regarding the results of the analyses did not arise in a significant percentage of cases.

In fact, it may occur that analyses have to be repeated, which means that the sample must be preserved for a given number of days prior to its disposal. Samples may also be preserved in the event of contestation by patients or, more generally speaking, for medical-legal reasons.

Test tubes containing already analyzed samples, obviously without the original seal, plug or screw cap, previously removed to enable penetration of the sampling needle, are collected in multiple supports which are hastily packed and placed in special cold storage compartments. Therefore, the prevention of fluid spills is left up to the adherence of plastic wrap or precarious coverings wrapped all around the support. The risk of spillage or leaks in the event of an accident is thus very high, as is the risk of personnel being contaminated by sometimes dangerously infected samples.

BRIEF SUMMARY OF THE INVENTION

To avoid this and other problems, a system has been devised to RESEAL test tubes of any type and size containing already analyzed samples, after the analysis itself and prior to storage, in order that the test tube container can be handled in complete safety. This solution is obviously also useful for the disposal of waste from hospitals or laboratories which, when open test tubes are involved, can create hazards for personnel who manually transfer such products from the laboratory to waste containers.

These and other aims are accomplished by the device of the present invention, basically consisting in a cap to be applied on the mouth of the test tube. The cap is composed of a piece of aluminum foil, which may be of different shapes, such as to adhere, following a heat sealing process, to the edge or side or both test tube surfaces, thereby sealing it perfectly. The adhesion of the aluminum cap to the glass or plastic of the test tube is achieved thanks to special adhesive lacquers present on the contact surface of the aluminum foil. A similar lacquer can also be applied on the top surface of the cap so that in the unlikely, but not impossible event of the sample undergoing further analyses, the same test tube can again be perforated using the sampling needle and later RESEALED.

In a second implementation of the invention, the sealed closure of the test tube could be achieved using a paper, plastic or metal label and a cold or hot gluing procedure. This solution is applicable, as previously illustrated, for the heat-sealing aluminum cap.

BRIEF DESCRIPTION OF THE SEVERAL VIEWS OF THE DRAWINGS

These and other characteristics will now be further clarified in relation to a simple design configuration of the invention. The description herein serves purely illustrative purposes and does not restrict the scope of this patent. Reference is made to the enclosed drawings.

DETAILED DESCRIPTION OF THE INVENTION

Figure 1:
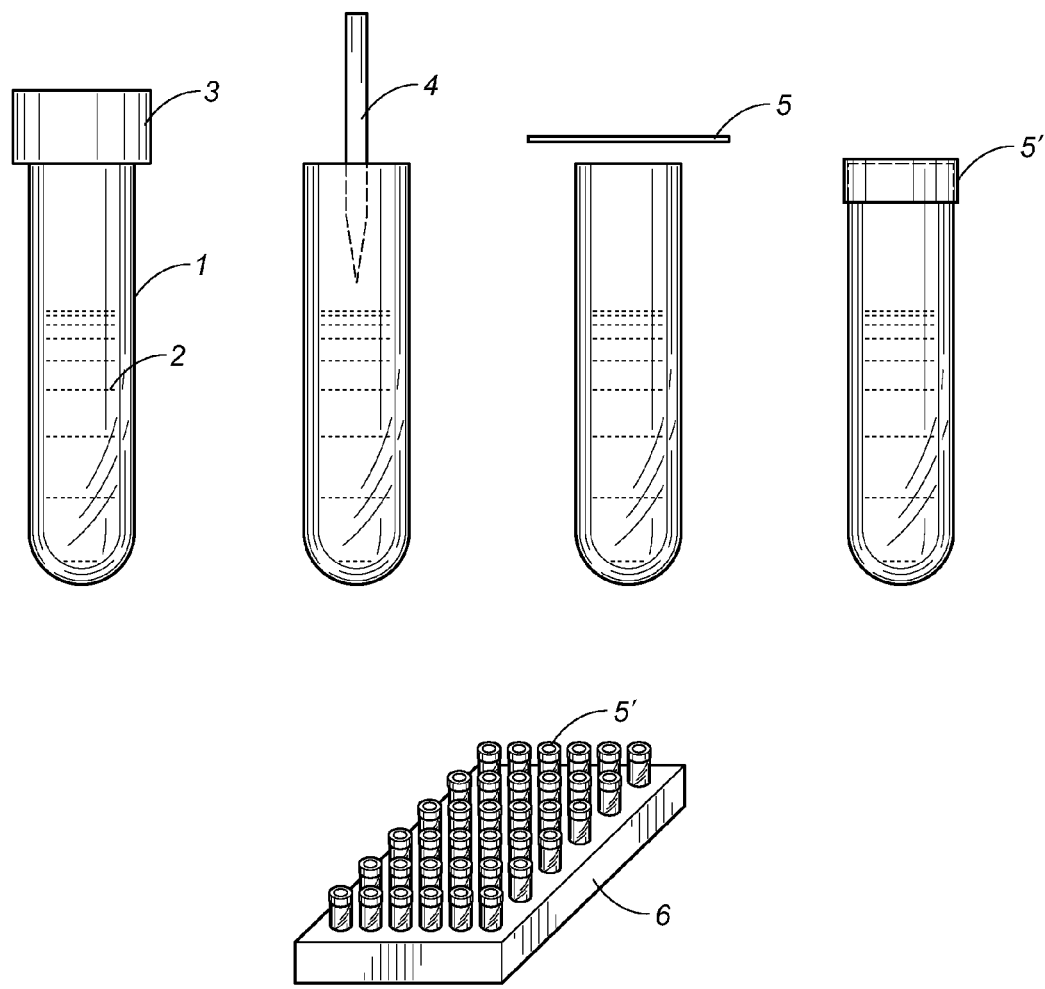
FIG. 1 is a schematic view approximately illustrating the sequence of operations.
Figure 2:
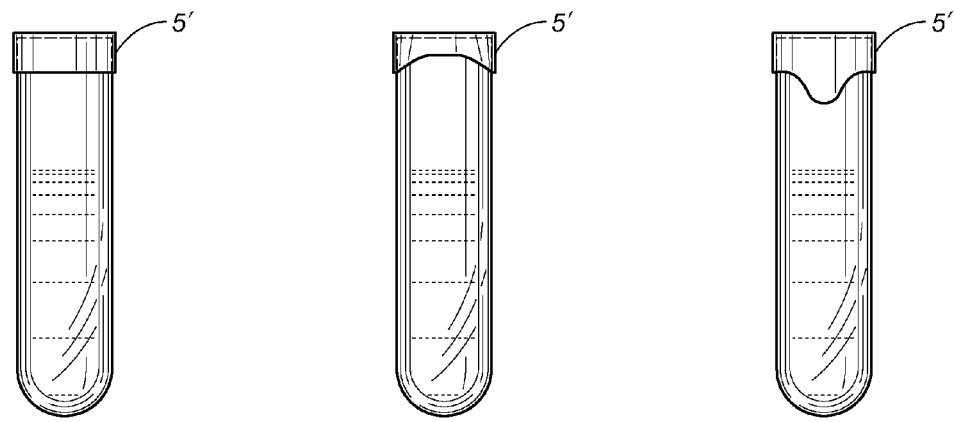
FIGS. 2-4 are schematic views showing the aluminum foil, constituting the cap applied on a test tube, viewed in cross section and from above, in three different shapes.
Figure 3:
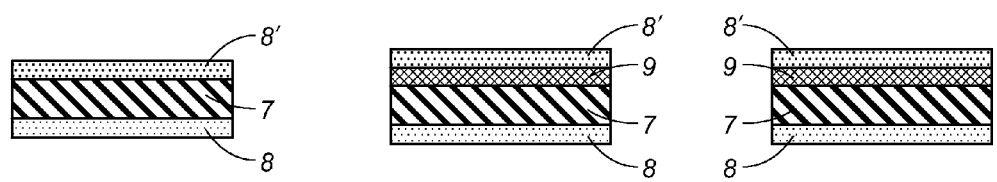
Figure 4:
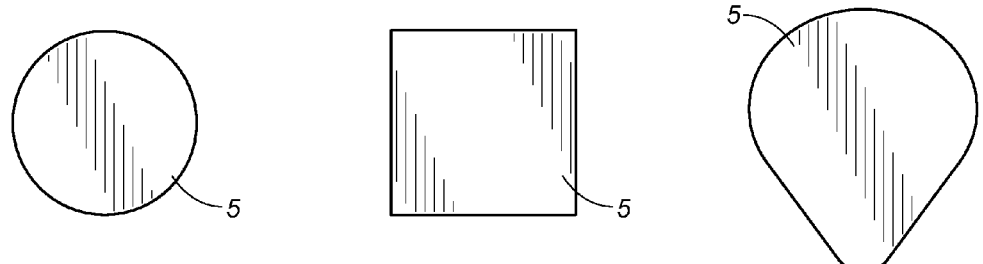
Figure 5:
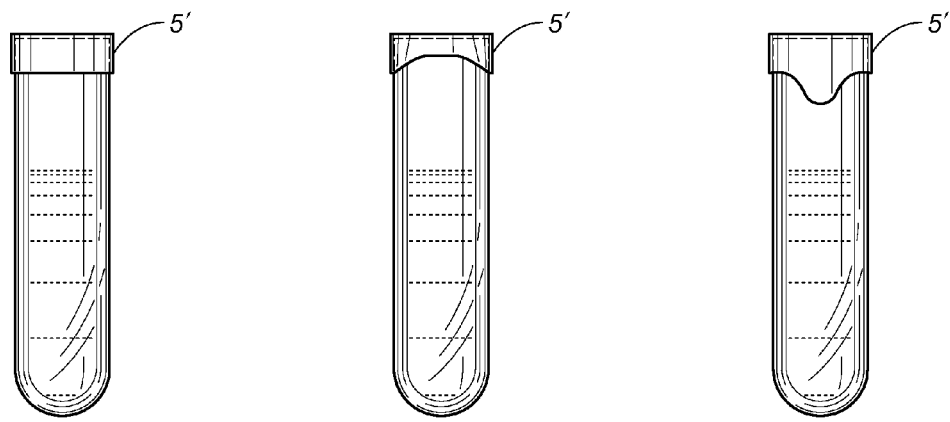
FIGS. 5-7 are schematic view showing the layer of paper constituting the label applied on a test tube, viewed in cross section and from above, in three different shapes.
Figure 6:
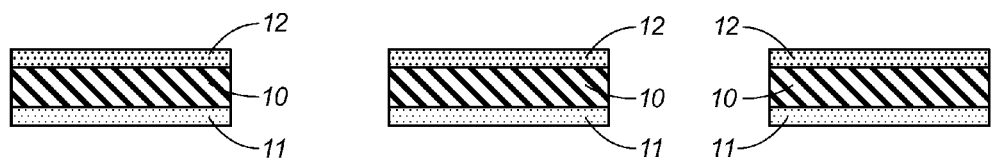
Figure 7:
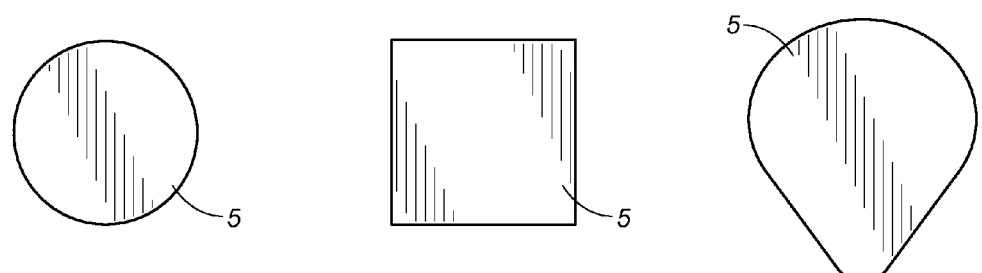

FIG. 1 indicates the test tube 1 containing the sample 2,3 and the original cap. FIG. 1' shows the test tube with its original cap removed so that the sampling needle 4 can penetrate it, and FIG. 1" shows the analyzed test tube surmounted by cap 5. FIG. 1''' shows the test tube RESEALED by cap 5', sealed and possibly moulded over the mouth.

The other figures indicate the container 6 of reseated test tubes ready for refrigeration, the layer 7 of aluminum forming the body of the cap, the bottom layer 8 of lacquer, the ink layer 9 of the stamp, and the top layer 8' of lacquer.

The figures also indicate the paper or plastic label 10, the layer of glue 11 on the underside, and the stamped ink layer 12.

I claim:

1. An assembly used in clinical analysis comprising:
a test tube having an open mouth at one end and a side surface extending therefrom, said open end having an edge extending therearound; and
an outer cap formed of a deformable aluminum foil positioned on said open mouth so as to cover said open mouth in gas-tight relationship therewith, said outer cap wrapping around said side surface of said test tube adjacent said open mouth, said outer cap having an adhesive heat-sealed first lacquer on a surface of said foil in contact with said edge of said open mouth and with said side surface, said outer cap having a second lacquer on an opposite surface of said foil, said first lacquer being of a material identical to a material of said second lacquer, said second lacquer being in direct contact with said foil, said material of said first lacquer being compatible with a material of said test tube, said outer cap being entirely closed over an area defined by said edge of said open end.

* * * * *